United States Patent
Krasnov

[11] 3,943,931
[45] Mar. 16, 1976

[54] GONIOLENS

[76] Inventor: Mikhail Mikhailovich Krasnov, ulitsa Veshina, 30, kv. 12, Moscow, U.S.S.R.

[22] Filed: Nov. 4, 1974

[21] Appl. No.: 520,872

Related U.S. Application Data

[63] Continuation of Ser. No. 427,130, Dec. 21, 1973, abandoned.

[52] U.S. Cl. .......................................... 128/303.1
[51] Int. Cl.² ........................................ A61B 17/36
[58] Field of Search ........ 128/303.1, 395, 396, 397, 128/329; 351/6, 16

[56] References Cited
UNITED STATES PATENTS

| | | | |
|---|---|---|---|
| 3,467,099 | 9/1969 | Lotmar | 128/303.1 |
| 3,589,800 | 6/1971 | Cardona | 351/16 |
| 3,630,602 | 12/1971 | Herbert | 351/16 |

OTHER PUBLICATIONS

Worst – American Journal of Ophthamology, Feb., 1968, pp. 251–254.
Bausch & Lomb – Allen Gonioscope Prism Sept. 23, 1947, pp. 1–7.

*Primary Examiner*—Lawrence W. Trapp
*Attorney, Agent, or Firm*—Holman & Stern

[57] ABSTRACT

A goniolens is defined as an oblique-truncated cylinder. The base of the cylinder has a concave surface to ensure complete contact thereof with the cornea of the eye. The truncated surface of the cylinder is convex and its curvature radius is equal to 8.5 mm. The angle confined by a planes of the concave and convex surfaces ranges from 20° to 60°, which makes it possible to focus the laser beam in the corner of the anterior segment of the eye during laser goniopuncture.

1 Claim, 6 Drawing Figures

GONIOLENS

This is a continuation of application Ser. No. 427,130 filed December 21, 1973 now abandoned.

BACKGROUND OF THE INVENTION

The present invention relates to eye microsurgery and more particularly, to a goniolens employed for examination and micromanipulations in the zone of the corner of the eye anterior segment.

PRIOR ART

A goniolens is known which is defined as an oblique-truncated cylinder whose base has a concave surface of a certain curvature radius to ensure complete contact with the cornea of the eye, while the truncated surface is convex (cf. Inventor's Certificate No. 118,573; Cl. A 61F 09/06/.

The parameters of the conventional lens are such that it can be used only for effecting visual control when manipulating with surgical instruments in the zone of the corner of the eye anterior segment, and do not provide for focusing and transfer of necessary energy of a laser beam without damaging the cornea during laser gonipuncture.

OBJECT AND SUMMARY OF THE INVENTION

An object of the present invention is to provide a goniolens that can be used during laser goniopuncture.

This object is accomplished in that in a goniolens defined as an oblique-truncated cylinder whose base has a concave surface of a curvature radius to ensure complete contact with the cornea of the eye, and the truncated surface is convex, according to the invention, the curvature radius of the convex surface is 8.5 mm, and the angle between the planes of the concave and convex surfaces ranges from 20° to 60°, which makes it possible to focus the laser beam on the corner of the eye anterior segment during laser goniopuncture.

The goniolens according to the present invention makes it possible to focus and transfer necessary energy of the laser beam to the area to be treated.

The following description of an exemplary embodiment of the present invention is given with reference to the accompanying drawings, in which:

DETAILED DESCRIPTION OF THE DRAWING

Figure 3:
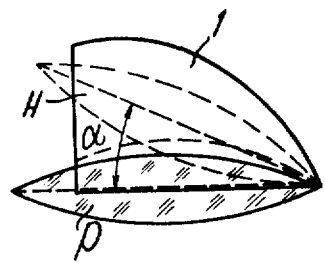
FIG. 3 is a side view of the goniolens.
Figure 1:
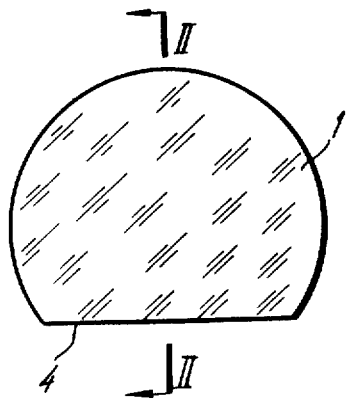
FIG. 1 is a front view of a goniolens being mounted onto the eye.
Figure 2:
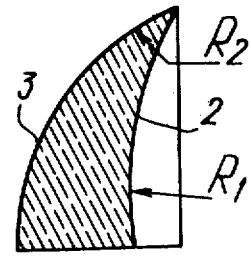
FIG. 2 is a section taken along line II—II in FIG. 1, the view looking in the direction of the arrows.

A goniolens 1 (FIG. 1) used for laser gonipuncture is defined as an oblique-truncated cylinder whose base has a concave surface 2 (FIG. 2) of a curvature radius $R_1$ equal to 8.5 mm. A truncated surface 3 of the lens 1 is convex, and its radius of curvature $R_2$ is also equal to 8.5 mm. The angle $\alpha$ (FIG. 3) confined by planes P and H of the concave and convex surfaces 2 and 3 is equal in this particular case to 40°C.

The angle $\alpha$ may vary from 20° to 60°, which makes it possible to use the goniolens in the corner of the eye anterior segment, and the ratio between structures of the corner of the anterior segment and batching of energy density in the area being treated may be different.

Figure 4:
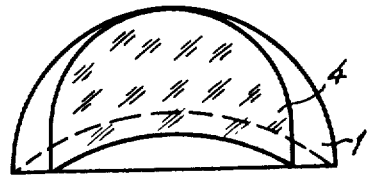
FIG. 4 is a bottom view of the goniolens.

The goniolens 1 has a longitudinal cut 4 (FIG. 4) which has a holder 5 (FIG. 5) fixed thereon. The portion of the holder 5 facing eye 6 has a peg 7 directing a filtering area 8 (FIG. 6) of the eye towards a laser beam 9 irradiated by a laser source 10 (FIG. 5) which is essentially a ruby crystal. The laser beam 9 is traversed into the goniolens 1 with the aid of a mirror 11.

Figure 6:
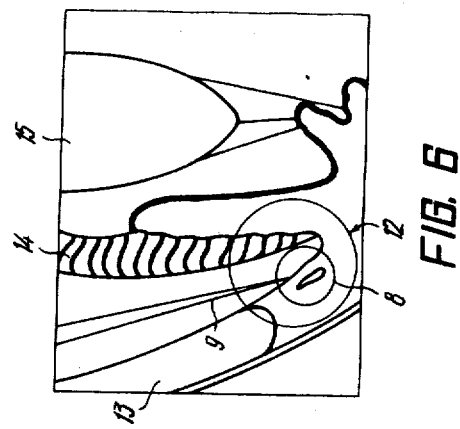
FIG. 6 is a view showing the structure of the corner of the eye anterior segment.

FIG. 6 shows an enlarged view of a fragment of the eye diagram, showing a corner 12 of the eye 6 anterior segment, a part of the cornea 13, iris 14 and crystalline lens 15.

Figure 5:
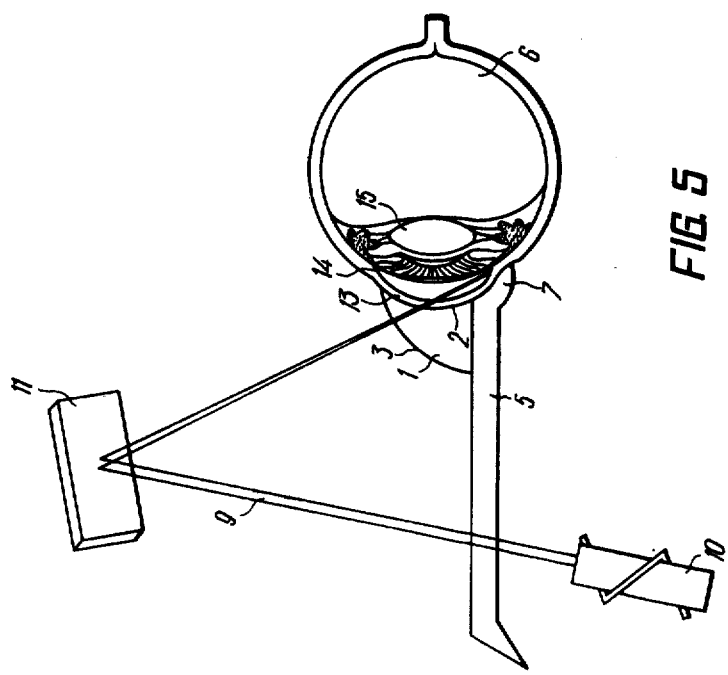
FIG. 5 is a view showing the path of the laser beam traversed during laser goniopuncture by employing the goniolens.

The goniolens 1 (FIG. 5) is mounted with its concave surface 2 onto the cornea 13 of the eye 6 in such a way that these two surfaces are brought into complete contact. Thus, the peg 7 of the holder 5 presses upon the filtering area 8 (FIG. 6) and turns the latter to provide the optimum angle of incidence of the laser beam 9 onto the area 8 on which the beam 9 is focussed by the lens 1 (FIG. 5). By distructing the tissue of the filtering area 8, the laser pulse attributes to drainage of the moisture to be found inside the segment.

The goniolens according to the present invention ensures transfer of the laser beam energy into the angle of the eye anterior segment with minimal losses and precise focusing of the area to be treated. The lens provides for passage of the laser beam without damaging the cornea of the eye and, therefore, can be successfully used for honioscopy of the eye. Besides, the lens is extremely convenient in practical use and does not require any additional skill on the part of its operators.

What we claim is:

1. A convex-concave contact lens with converging optical surfaces for use in laser microsurgery of the eye, said lens having a concave surface of a curvature radius to ensure complete contact thereof with the cornea of the eye and a truncated convex surface of a curvature radius equal to 8.5 mm, the angle confined by the planes of the concave and convex surfaces ranging from 20° to 60°, whereby it is possible to focus a laser beam through said lens in the corner of the anterior segment of the eye during laser goniopuncture.

* * * * *